(12) United States Patent
Coalter, III et al.

(10) Patent No.: US 8,633,126 B2
(45) Date of Patent: *Jan. 21, 2014

(54) THREE AND FOUR ATOM BRIDGED DICARBONATE COMPOUNDS AS INTERNAL DONORS IN CATALYSTS FOR POLYPROPYLENE MANUFACTURE

(75) Inventors: Joseph N. Coalter, III, Lake Jackson, TX (US); Tak W. Leung, Houston, TX (US); Tao Tao, Houston, TX (US); Kuanqiang Gao, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 370 days.

This patent is subject to a terminal disclaimer.

(21) Appl. No.: 12/956,091

(22) Filed: Nov. 30, 2010

(65) Prior Publication Data
US 2011/0130529 A1 Jun. 2, 2011

Related U.S. Application Data

(60) Provisional application No. 61/265,934, filed on Dec. 2, 2009.

(51) Int. Cl.
*C08F 4/02* (2006.01)
*C08F 2/00* (2006.01)
*C07C 69/96* (2006.01)

(52) U.S. Cl.
USPC ........................... 502/125; 526/213; 558/268

(58) Field of Classification Search
USPC .................................. 502/127; 526/213, 216
See application file for complete search history.

(56) References Cited

U.S. PATENT DOCUMENTS

| | | | |
|---|---|---|---|
| 3,214,469 A | 10/1965 | Green et al. | |
| 4,442,276 A | 4/1984 | Kashiwa et al. | |
| 4,460,701 A | 7/1984 | Terano et al. | |
| 4,540,679 A | 9/1985 | Arzoumanidis et al. | |
| 4,547,476 A | 10/1985 | Terano et al. | |
| 4,579,836 A | 4/1986 | Arzoumanidis et al. | |
| 4,612,299 A | 9/1986 | Arzoumanidis et al. | |
| 4,710,482 A | 12/1987 | Job | |
| 4,816,433 A | 3/1989 | Terano et al. | |
| 4,829,037 A | 5/1989 | Terano et al. | |
| 4,866,022 A | 9/1989 | Arzoumanidis et al. | |
| 4,927,797 A | 5/1990 | Ewen | |
| 4,946,816 A | 8/1990 | Cohen et al. | |
| 4,990,479 A | 2/1991 | Ishimaru et al. | |
| 5,028,671 A | 7/1991 | Kioka et al. | |
| 5,034,361 A | 7/1991 | Job et al. | |
| 5,066,737 A | 11/1991 | Job | |
| 5,066,738 A | 11/1991 | Ewen | |
| 5,077,357 A | 12/1991 | Job | |
| 5,082,907 A | 1/1992 | Job | |
| 5,106,806 A | 4/1992 | Job | |
| 5,146,028 A | 9/1992 | Job | |
| 5,151,399 A | 9/1992 | Job | |
| 5,153,158 A | 10/1992 | Kioka et al. | |
| 5,229,342 A | 7/1993 | Job | |
| 5,247,031 A | 9/1993 | Kioka et al. | |
| 5,247,032 A | 9/1993 | Kioka et al. | |
| 6,825,146 B2 | 11/2004 | Kilty et al. | |
| 7,491,670 B2 | 2/2009 | Chen et al. | |
| 7,491,781 B2 | 2/2009 | Uhrhammer et al. | |
| 8,263,520 B2 * | 9/2012 | Coalter et al. | ................ 502/127 |
| 2005/0244746 A1 | 11/2005 | Makino et al. | |
| 2008/0103191 A1 | 5/2008 | Hansen et al. | |

FOREIGN PATENT DOCUMENTS

| | | |
|---|---|---|
| GB | 1364505 A | 8/1974 |
| WO | WO-2005030815 A1 | 4/2005 |
| WO | WO-2005100363 A1 | 10/2005 |
| WO | WO-2009029447 A1 | 3/2009 |
| WO | WO-2009029486 A2 | 3/2009 |
| WO | WO-2009029487 A1 | 3/2009 |
| WO | WO-2009085649 A1 | 7/2009 |

OTHER PUBLICATIONS

Kuwano, Ryoichi. Kusano, Hiroki. "Benzyl Protection of Phenols under Neutral Conditions: Palladium-Catalyzed Benzylations of Phenols." Organic Letters. vol. 10, No. 10. Apr. 11, 2008. 1979-1982.*

International Search Report and Written Opinion (PCT/US2010/058273).

Hanselaer, R., L. D'Haenens, M. Martens, H. Van Nieuwenhuyse, and C.F. Van Sumere. "N-Acylamino Acids and Peptides. VII. Synthesis of Oxygen-Sensitive N-Acylglycines (N-Caffeoylglycine, N-Protocatechuoylglycin E and N-Galloylglycine) and a N-Acyldipeptide (N-Caffeoylglycyl-L-Phenylalanin." *Bulletin Des societies Chimiques Belges.* 92.11-12 (1983): 1029-1038.

Muller E et al: "Stabile ortho-Semichinonsalze" Justus Liebigs Annalen Der Chemie, Verlag Chemie GmbH, Weinheim; DE, vol. 688, Jan. 1, 1965, pp. 134-149, XP002584430.

(Continued)

*Primary Examiner* — David W Wu
*Assistant Examiner* — Elizabeth Eng

(57) ABSTRACT

A solid, hydrocarbon-insoluble, catalyst component useful in polymerizing olefins, said catalyst component containing magnesium, titanium, and halogen, and further containing an internal electron donor having a structure:

$$[R_1-O-C(O)-O-]_xR_2$$

wherein $R_1$ is independently at each occurrence, an aliphatic or aromatic hydrocarbon, or substituted hydrocarbon group containing from 1 to 20 carbon atoms; x is 2-4; and $R_2$ is an aliphatic or aromatic hydrocarbon, or substituted hydrocarbon group containing from 1 to 20 carbon atoms, provided that there are from 3 to 4 atoms in the shortest chain connecting a first $R_1$—O—C(O)—O— group and a second $R_1$—O—C(O)—O— group.

18 Claims, No Drawings

(56) References Cited

OTHER PUBLICATIONS

Murata, Kazuo, Kazuo Noda, Keiichi Kohno, and Masayoshi Samejima. "Bioavailabilty and Pharmacokinetics of an Oral Dopamine Prodrug in Dogs." *Journal of Pharmaceutical Sciences*. 78.10 (1989): 812-14.

Rosemund and Theodor Boehm K. W: "Zur Kenntnis der Polyoxy-Benzylalkohole, insbesondere des Gallusalkohols and eines daraus gewonnenen Gerbstoffes", Archiv Der Pharmazie, Wiley-VCH Verlag GmbH & Co. KGAA, DE, vol. 264, No. 26-43, Jan. 1, 1926, pp. 448-459.

Stenseth, Raymond E., Robert M. Schisla, and Joseph W. Baker. "Halophenyl and 8-Quinolyl Carbonates." *Journal of Chemical and Engineering Data*. 9.3 (1964): 390-97.

Veldurthy, Bhaskar, Jean-Marc Clacens, and Francois Figueras. "Correlation Between the Basicity of Solid Bases and their Catalytic Activity Towards the Synthesis of Unsymmetrical Organic Carbonates." *Jornal of Catalysis*. 229.1 (2005): 237-42.

Kiji, Jitsuo, Tamon Okano, Eiichi Fujii, and Jiro Tsuji. "A Simple Synthetic Method to Bis(Methylene)Butanedioates." *Synthesis*. (1997): 869-70.

Kuwano, Ryoichi, and Hiroki Kusano. "Benzyl Protection of Phenols under Neutral Conditions: Palladium-Catalyzed Benzylations of Phenols." *Organic Letters*. 10.10 (2008): 1979-82.

\* cited by examiner

THREE AND FOUR ATOM BRIDGED DICARBONATE COMPOUNDS AS INTERNAL DONORS IN CATALYSTS FOR POLYPROPYLENE MANUFACTURE

This application is a non-provisional application claiming priority from the U.S. Provisional Patent Application No. 61/265,934, filed on Dec. 2, 2009, entitled "THREE AND FOUR ATOM BRIDGED DICARBONATE COMPOUNDS AS INTERNAL DONORS IN CATALYSTS FOR POLYPROPYLENE MANUFACTURE," the teachings of which are incorporated by reference herein, as if reproduced in full hereinbelow.

This invention relates to components useful in propylene polymerization catalysts, and particularly relates to electron donor components used in combination with magnesium-containing supported titanium-containing catalyst components.

BACKGROUND AND SUMMARY OF THE INVENTION

Use of solid, transition metal-based, olefin polymerization catalyst components is well known in the art including such solid components supported on a metal oxide, halide or other salt such as widely-described magnesium-containing, titanium halide-based catalyst components. Such catalyst components are commonly referred to as "supported". Although many polymerization and copolymerization processes and catalyst systems have been described for polymerizing or copolymerizing alpha-olefins, it is advantageous to tailor a process and catalyst system to obtain a specific set of properties of a resulting polymer or copolymer product. For example, in certain applications, a combination of acceptably high activity, good morphology, desired particle size distribution, acceptable bulk density, and the like are required together with polymer characteristics such as stereospecificity, molecular weight distribution, and the like.

Typically, supported catalyst components useful for polymerizing propylene and higher alpha-olefins, as well as for polymerizing propylene and higher olefins with minor amounts of ethylene and other alpha-olefins contain an internal electron donor component. Such internal electron donor is an integral part of the solid supported catalyst component and is distinguished from an external electron donor component, which together with an aluminum alkyl component, typically comprises the catalyst system. While the internal electron donor is an integral part of the solid supported component, the external electron donor may be combined with the solid supported component shortly before the combination is contacted with an olefin monomer or in the presence of olefin monomer. The external electron donor is commonly referred to as a selectivity control agent (or "SCA"), and the supported catalyst component is commonly referred to as a procatalyst.

Selection of the internal electron donor can affect catalyst performance and the resulting polymer formed from a catalyst system. Generally, organic electron donors have been described as useful in preparation of the stereospecific supported catalyst components including organic compounds containing oxygen, nitrogen, sulfur, and/or phosphorus. Such compounds include organic acids, organic acid anhydrides, organic acid esters, alcohols, ethers, aldehydes, ketones, amines, amine oxides, amides, thiols, various phosphorus acid esters and amides, and the like. Mixtures of organic electron donors have been described as useful when incorporated into supported catalyst components. Examples of organic electron donors include dicarboxy esters such as alkyl phthalate and succinate esters.

In current practice, alkyl phthalate esters are commonly used as internal electron donors in commercial propylene polymerization catalyst systems. However, certain environmental questions have been raised concerning continued use of phthalate derivatives in applications where human contact is anticipated.

Particular uses of propylene polymers depend upon the physical properties of the polymer, such as molecular weight, viscosity, stiffness, flexural modulus, and polydispersity index (molecular weight distribution (Mw/Mn)). In addition, polymer or copolymer morphology often is critical and typically depends upon catalyst morphology. Good polymer morphology generally involves uniformity of particle size and shape, resistance to attrition and an acceptably high bulk density. Minimization of very small particles (fines) typically is important especially in gas-phase polymerizations or copolymerizations in order to avoid transfer or recycle line pluggage.

The art presently recognizes a finite set of compounds suitable for use as internal electron donors in supported catalyst components. With the continued diversification and sophistication of applications for olefin-based polymers, the art recognizes the need for olefin-based polymers with improved and varied properties. Desirable would be internal electron donors in supported catalyst components that contribute to strong catalyst activity and high hydrogen response during polymerization. Further desired are internal electron donors in supported catalyst components that produce propylene-based polymers with high isotacticity, commonly expressed as a xylenes soluble fraction (XS) and/or final melting temperature (TMF).

The invention described relates to use of an internal modifier (internal electron donor) in a propylene polymerization catalyst component, which contains at least two carbonate functionalities.

Accordingly, one embodiment of the invention is a solid, hydrocarbon-insoluble, catalyst component useful in polymerizing olefins, said catalyst component containing magnesium, titanium, and halogen, and further containing an internal electron donor comprising a compound having a structure:

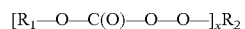

$$[R_1\text{—O—C(O)—O—O—}]_xR_2$$

wherein $R_1$ is independently at each occurrence, an aliphatic or aromatic hydrocarbon, or substituted hydrocarbon group containing from 1 to 20 carbon atoms; x is 2-4; and $R_2$ is an aliphatic or aromatic hydrocarbon, or substituted hydrocarbon group containing from 1 to 20 carbon atoms, provided that there are from 3 to 4 atoms in the shortest chain connecting a first $R_1$—O—C(O)—O— group and a second $R_1$—O—C(O)—O— group.

DETAILED DESCRIPTION OF THE INVENTION

Definitions

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate.

The term "composition," as used herein, includes a mixture of materials which comprise the composition, as well as reaction products and decomposition products formed from the materials of the composition.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term "interpolymer," as used herein, refers to polymers prepared by the polymerization of at least two different types of monomers. The generic term interpolymer thus includes copolymers, usually employed to refer to polymers prepared from two different monomers, and polymers prepared from more than two different types of monomers.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term, "ethylene-based polymer," as used herein, refers to a polymer that comprises a majority weight percent polymerized ethylene monomer (based on the total weight of polymerizable monomers), and optionally may comprise at least one polymerized comonomer.

The term, "propylene-based polymer," as used herein, refers to a polymer that comprises a majority weight percent polymerized propylene monomer (based on the total amount of polymerizable monomers), and optionally may comprise at least one polymerized comonomer.

As used herein, the term "hydrocarbyl" and "hydrocarbon" refer to substituents containing only hydrogen and carbon atoms, including branched or unbranched, saturated or unsaturated, cyclic, polycyclic, fused, or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

As used herein, the terms "substituted hydrocarbyl" and "substituted hydrocarbon" refer to a hydrocarbyl group that is substituted with one or more nonhydrocarbyl substituent groups. A nonlimiting example of a nonhydrocarbyl substituent group is a heteroatom. As used herein, a "heteroatom" refers to an atom other than carbon or hydrogen. The heteroatom can be a non-carbon atom from Groups IV, V, VI, and VII of the Periodic Table. Nonlimiting examples of heteroatoms include: halogens (F Cl, Br, I), N, O, P, B, S, and Si. A substituted hydrocarbyl group also includes a halohydrocarbyl group and a silicon-containing hydrocarbyl group. As used herein, the term "halohydrocarbyl" group refers to a hydrocarbyl group that is substituted with one or more halogen atoms.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 to 20 carbon atoms.

The term "substituted alkyl," as used herein, refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, haloalkyl, hydroxy, amino, phosphido, alkoxy, amino, thio, nitro, other heteroatom containing groups, and combinations thereof. Suitable substituted alkyls include, for example, benzyl, trifluoromethyl and the like.

The term "aryl," as used herein, refers to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. The aryls have 6 to 20 carbon atoms.

The term "carbonate" as used herein, refers to a functional group within a larger molecule that contains a carbon atom bound to three oxygen atoms, one of which is double bonded. Such compounds are also known as organocarbonates or carbonate esters.

The supported catalyst components of this invention contain at least one internal electron donor comprising electron donating substituents comprising a dicarbonate. Dicarbonates are defined as those compounds corresponding to the following structure:

$$[R_1-O-C(O)-O-]_xR_2$$

wherein $R_1$ is independently at each occurrence, an aliphatic or aromatic hydrocarbon, or substituted hydrocarbon group containing from 1 to 20 carbon atoms; x is 2-4; and $R_2$ is an aliphatic or aromatic hydrocarbon, or substituted hydrocarbon group containing from 1 to 20 carbon atoms, provided that there are from 3 to 4 atoms in the shortest chain connecting a first $R_1$—O—C(O)—O— group and a second $R_1$—O—C(O)—O— group.

It is preferred that x be equal to 2, and as a result, in the broadest sense of the invention the term "dicarbonate" is used to generically describe these compounds even though compounds with 3 or even 4 carbonate groups are contemplated.

For many applications it is preferred that the $R_1$ group be an aliphatic hydrocarbon group. It is also preferred that such aliphatic group be of relatively shorter length, for example from 1-6 carbon atoms, with 2, 3, or 4 carbon atoms being the most preferred.

The $R_2$ groups in the dicarbonates useful in the present invention are such that there are 3 to 4 atoms in the shortest chain between 2 carbonate groups. Preferably, these linking atoms are carbon atoms but heteroatoms such as oxygen, nitrogen, silicon, or phosphorous may also be used. It should be understood that the "3 to 4" linking atoms refers only to the atoms in the shortest chain between the carbonate groups and that the $R_2$ groups are typically much larger, as they contain atoms which do not directly link the carbonate groups. Preferred $R_2$ groups include biphenyls where the linking atoms include the bridge between the phenyl rings, and naphthalenes, where the linking atoms include at least one of the shared carbon atoms of the fused rings. Such biphenyls or naphthalenes may advantageously contain alkyl groups or other substituents.

The hydrocarbons useful in the present invention may be substituted with atoms other than carbon or hydrogen. For example, alkyl groups used in this invention may be substituted with compatible groups containing heteroatoms including nitrogen, oxygen, phosphorus, silicon, and halogens. Thus, a hydrocarbon group used in this invention may be substituted with an ether, amine, amide, chloro, bromo, or silyl group, for example. Similarly, cyclic structures which may be incorporated into the donor compounds as part of either the $R_1$ or $R_2$ groups may contain hetero atoms, such as nitrogen, oxygen, silicon, and phosphorus.

Non-limiting examples of some specific dicarbonates for use in the present invention include the following, and their substituted derivatives:

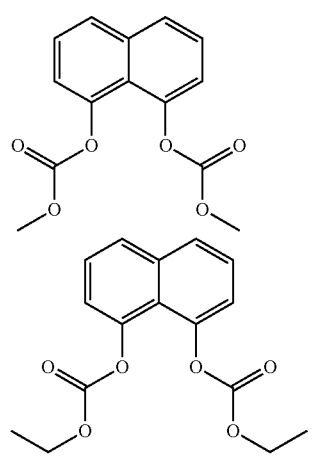

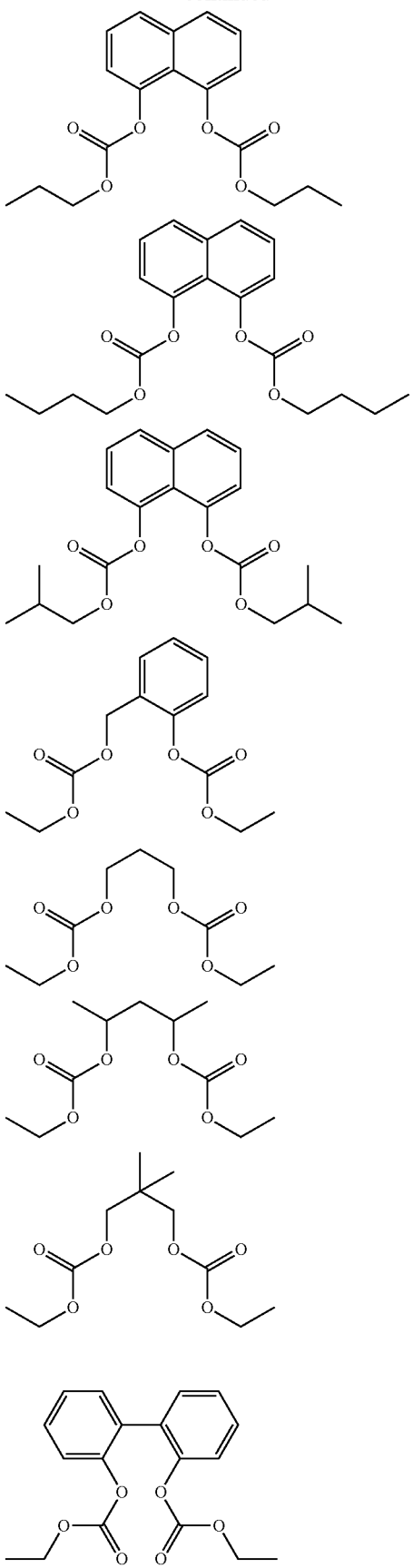

-continued

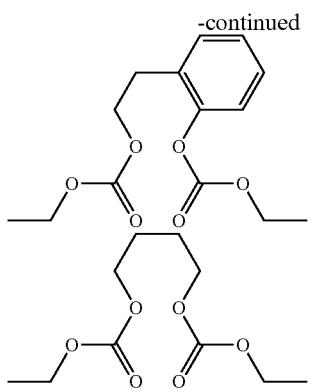

The dicarbonate materials suitable for use as internal electron donors in the present invention can be made according to methods known in the art. One suitable method for making a true dicarbonate (that is, where x=2) involves reacting a diol with at least two molar equivalents of a substituted cholorformate. Thus the reaction could be described as:

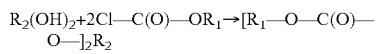

where $R_1$ and $R_2$ are as described above. A suitable base may be present to sequester the hydrochloric acid liberated during the reaction. A suitable variation of this method is to first react the diol with a suitable base to effect partial or complete deprotonation, followed by treatment with at least 2 molar equivalents of a substituted cholorformate.

The dicarbonates of the present invention are useful as internal electron donors in high activity supported titanium-containing Ziegler-Natta catalysts commonly used in the manufacture of polypropylene.

Supported titanium-containing components useful in this invention generally are supported on hydrocarbon-insoluble, magnesium-containing compounds in combination with an electron donor compound. Such supported titanium-containing olefin polymerization catalyst component typically is formed by reacting a titanium (IV) halide, an organic electron donor compound and a magnesium-containing compound. Optionally, such supported titanium-containing reaction product may be further treated or modified by further chemical treatment with additional electron donor or Lewis acid species. The resulting supported titanium-containing components are also referred to as "supported catalyst components" or "procatalysts."

Suitable magnesium-containing compounds include magnesium halides; a reaction product of a magnesium halide such as magnesium chloride or magnesium bromide with an organic compound, such as an alcohol or an organic acid ester, or with an organometallic compound of metals of Groups I-III; magnesium alcoholates; mixed magnesium/titanium halide alcoholates; or magnesium alkyls.

Examples of supported catalyst components are prepared by reacting a magnesium chloride, alkoxy magnesium chloride or aryloxy magnesium chloride, or mixed magnesium/titanium halide alcoholate with a titanium halide, such as titanium tetrachloride, and further incorporation of an electron donor compound. In a preferable preparation, the magnesium-containing compound is dissolved, or is in a slurry, in a compatible liquid medium, such as a hydrocarbon or halogenated hydrocarbon to produce suitable catalyst component particles.

The possible supported catalyst components listed above are only illustrative of many possible solid, magnesium-containing, titanium halide-based, hydrocarbon-insoluble catalyst components useful in this invention and known to the art. This invention is not limited to a specific supported catalyst component.

Supported catalyst components known to the art may be used with the internal donors described in this invention. Typically, the internal electron donor material of this invention is incorporated into a solid, supported catalyst component during formation of such component. Typically, such electron donor material is added with, or in a separate step, during treatment of a solid magnesium-containing material with a suitable titanium source, such as a titanium (IV) compound. Such magnesium-containing material typically is in the form of discrete particles and may contain other materials such as transition metals and organic compounds. Also, a mixture of magnesium chloride, titanium tetrachloride and the internal donor may be formed into a supported catalyst component by ball-milling.

Magnesium Source

The magnesium source is preferably in the form of a supported catalyst component precursor prepared in accordance with any of the procedures described in, for example, U.S. Pat. Nos. 4,540,679; 4,612,299; 4,866,022; 4,946,816; 5,034,361; 5,066,737; 5,082,907; 5,106,806; 5,146,028; 5,151,399; 5,229,342 and 7,491,781. The magnesium source may also be a magnesium halide, alkyl, aryl, alkaryl, alkoxide, alkaryloxide or aryloxide, alcohol adducts thereof, carbonated derivatives thereof, or sulfonated derivatives thereof, but preferably is an alcohol adduct of a magnesium halide, a magnesium dialkoxide, a carbonated magnesium dialkoxide, a carbonated magnesium diaryloxide, or a mixed magnesium/titanium halide alcoholate. Magnesium compounds containing one alkoxide and one aryloxide group can also be employed, as well as magnesium compounds containing a halogen in addition to one alkoxide, alkaryloxide, or aryloxide group. The alkoxide groups, when present, most suitable contain from 1 to 8 carbons, preferably from 2 to 6 carbon atoms. The aryloxide groups, when present, most suitable contain from 6 to 10 carbons. When a halogen is present, it is preferably chlorine.

Among the magnesium dialkoxides and diaryloxides which can be employed are those of the formula $Mg(OC(O)OR^3)_a(OR^4)_{2-a}$ wherein $R^3$ and $R^4$ are alkyl, alkaryl, or aryl groups, and a is about 0.1 to about 2. The most preferable magnesium compound containing a carbonate group is carbonated magnesium diethoxide (CMEO), $Mg(OC(O)OEt)_2$. Optionally the magnesium may be halogenated with an additional halogenating agent, e.g., thionyl chloride or alkylchlorosilanes, prior to contact with the tetravalent titanium source.

A somewhat different type of magnesium source is described by the general formula $Mg_4(OR^5)_6(R^6OH)_{10}A$ in which each $R^5$ or $R^6$ is a lower alkyl of up to 4 carbon atoms inclusive and A is one or more anions having a total charge of −2. The manufacturing of this magnesium source is disclosed in U.S. Pat. No. 4,710,482 to Job which is incorporated herein by reference.

Another particularly preferred magnesium source is one that contains moieties magnesium and titanium and probably moieties of at least some of halide, alkoxide, and a phenolic compound. Such complex procatalyst precursors are produced by contacting a magnesium alkoxide, a titanium alkoxide, a titanium halide, a phenolic compound, and an alkanol. See U.S. Pat. No. 5,077,357 to Job which is incorporated herein by reference.

A further useful magnesium source is a mixed magnesium/titanium compound ("MagTi"). The "MagTi precursor" has the formula $Mg_bTi(OR^7)_cX^1_d$ wherein $R^7$ is an aliphatic or aromatic hydrocarbon radical having 1 to 14 carbon atoms or $COR^8$ wherein $R^8$ is an aliphatic or aromatic hydrocarbon radical having 1 to 14 carbon atoms; each $OR^7$ group is the same or different; $X^1$ is independently chlorine, bromine or iodine, preferably chlorine; b is 0.5 to 56, or 2 to 4; c is 2 to 116 or 5 to 15; and d is 0.5 to 116, or 1 to 3. These precursors are prepared by controlled precipitation through removal of an alcohol from the reaction mixture used in their preparation. As such, a reaction medium comprises a mixture of an aromatic liquid, especially a chlorinated aromatic compound, most especially chlorobenzene, with an alkanol, especially ethanol. Suitable halogenating agents include titanium tetrabromide, titanium tetrachloride or titanium trichloride, especially titanium tetrachloride. Removal of the alkanol from the solution used in the halogenation, results in precipitation of the solid precursor, having especially desirable morphology and surface area. Moreover, the resulting precursors are particularly uniform in particle size.

An additional useful magnesium source is a benzoate-containing magnesium chloride material ("BenMag"). As used herein, a "benzoate-containing magnesium chloride" ("BenMag") can be a supported catalyst component (i.e., a halogenated supported catalyst component precursor) which contains a benzoate internal electron donor. The BenMag material may also include a titanium moiety, such as a titanium halide. The benzoate internal donor is labile and can be replaced by other electron donors during the supported catalyst component and/or catalyst synthesis. Nonlimiting examples of suitable benzoate groups include ethyl benzoate, methyl benzoate, ethyl p-methoxybenzoate, methyl p-ethoxybenzoate, ethyl p-ethoxybenzoate, ethyl p-chlorobenzoate. A preferred benzoate group is ethyl benzoate. Nonlimiting examples of suitable BenMag procatalyst precursors include catalysts of the trade names SHAC™ 103 and SHAC™ 310 available from The Dow Chemical Company, Midland, Mich. The BenMag supported catalyst component precursor may be a product of halogenation of a supported catalyst component precursor (e.g., a magnesium dialkoxide, a carbonated magnesium dialkoxide, or a MagTi precursor) in the presence of a benzoate compound.

Titanium Source

The titanium source for the supported catalyst component preferably is a tetravalent titanium which contains at least two halogen atoms, and preferably contains four halogen atoms, e.g., $Ti(OR^9)_eX^2_{4-e}$, wherein $R^9$ is a hydrocarbon, and $X^2$ is a halide and e is 0 to 2. Most preferably these halogen atoms are chlorine atoms. Titanium compounds containing up to two alkoxy, alkaryloxy or aryloxy groups can be employed. The alkoxy groups, when present, most suitably contain from 1 to 8 carbon atoms, preferably 2 to 6 carbon atoms. The aryloxy or alkaryloxy groups, when present, most suitably contain from 6 to 12 carbon atoms, preferably from 6 to 10 carbon atoms. Examples of suitable alkoxy- and aryloxy-titanium halides include diethoxy titanium dibromide, isopropoxy titanium triiodide, dihexoxy titanium dichloride, and phenoxy titanium trichloride. The most preferable titanium source is $TiCl_4$.

Supported Catalyst Component Manufacture

The magnesium compound preferably is reacted (i.e., halogenated) with the tetravalent titanium halide in the presence of an internal electron donor and optionally a halohydrocarbon. Optionally, an inert hydrocarbon diluent or solvent also may be present. Various methods for preparing supported catalyst components are known in the art. Some of these methods are described in, for example, U.S. Pat. Nos. 4,442,276; 4,460,701; 4,547,476; 4,816,433; 4,829,037; 4,927,797; 4,990,479; 5,066,738; 5,028,671; 5,153,158; 5,247,031 and 5,247,032. Regardless of the method of formation, the supported catalyst components of this invention include the internal electron donor material described in this invention.

When optionally employed, the halohydrocarbon used may be aromatic, aliphatic, or alicyclic. Most preferably, the halogen of the halohydrocarbon is chlorine. Aromatic halohydrocarbons are preferred, particularly those containing from 6 to 12 carbon atoms, preferably 6 to 10 carbon atoms. Preferably such halohydrocarbons contain 1 or 2 halogen atoms, although more may be present if desired. Suitable aromatic halohydrocarbons include, but are not limited to chlorobenzene, bromobenzene, dichlorobenzene, dichlorodibromobenzene, chlorotoluene, dichlorotoluene, and chloronaphthalene. The aliphatic halohydrocarbons contain from 1 to 12 carbon atoms, preferably from 1 to 9 carbon atoms and at least 2 halogen atoms. Suitable aliphatic halohydrocarbons include, but are not limited to dibromomethane, trichloromethane, 1,2-dichloroethane, trichloroethane, dichlorofluoroethane, hexachloroethane, trichloropropane, chlorobutane, dichlorobutane, chloropentane, trichlorofluorooctane, tetrachloroisooctane, dibromodifluorodecane, carbon tetrachloride, and trichloroethane. The alicyclic halohydrocarbons which can be employed contain from 3 to 12 carbon atoms, and preferably from 3 to 9 carbon atoms, and at least 2 halogen atoms. Suitable alicyclic halohydrocarbons include dibromocyclobutane, and trichlorocyclohexane.

The optional inert hydrocarbon diluent may be aliphatic, aromatic or alicyclic. Some exemplary diluents are isopentane, n-octane, isooctane, xylene, or toluene.

Halogenation of the magnesium compound with the halogenated tetravalent titanium halide is effected employing an excess of the titanium halide. At least 2 moles of the titanium halide should be employed per mole of the magnesium compound. Preferably from about 4 moles to about 100 moles of the titanium halide are employed per mole of the magnesium compound, and most preferably from about 4 moles to about 20 moles of the titanium halide are employed per mole of the magnesium compound.

When optionally employed, the halohydrocarbon is used in an amount sufficient to dissolve the titanium halide and the internal electron donor, and to adequately disperse the magnesium compound. Usually the dispersion contains from about 0.005 to about 2.0 moles of the solid magnesium compound per mole of halohydrocarbon, preferably from about 0.01 to about 1.0 mole of the solid magnesium compound per mole of the halohydrocarbon. The internal electron donor is employed in an amount sufficient to provide a molar ratio of said compound to the titanium halide of from about 0.0005:1 to about 2.0:1, preferably from about 0.001:1 to about 0.1:1. About 1:100 to 100:1 by volume of halohydrocarbon to optional diluent may be used.

Halogenation can be effected at a temperature up to about 150° C., preferably from about 80° C. to about 140° C. Usually the reaction is allowed to proceed over a period of 0.1 to 6 hours, preferably between about 0.5 to about 3.5 hours. For convenience, halogenation is usually effected at atmospheric pressure, although a range of pressures can be employed, e.g., 0.5 atm (50,700 Pa) to 5 atm (507,000 Pa). The halogenated product, like the starting magnesium compound, is a solid material which can be isolated from the liquid reaction medium by drying, filtration, decantation, evaporation, distillation or any suitable method.

After separation, the halogenated product (also termed the supported catalyst component upon halogenation) may be treated one or more times with additional tetravalent titanium halide to remove residual alkoxy and/or aryloxy groups and maximize catalyst activity or other desired properties. Preferably, the halogenated product is treated at least twice with separate portions of the tetravalent titanium halide. Generally, the reaction conditions employed to treat the halogenated product with the titanium halide are the same or similar to those employed during the initial halogenation of the magnesium compound, and the internal electron donor may or may not be present during the treatment(s). When optionally employed, the halohydrocarbon is typically used to dissolve the titanium halide and disperse the solid, halogenated product. If desired, the halogenated product may be treated with the acid halide before or after it is treated with the titanium compound for the second time. From 5 mmol to 200 mmol of the acid halide generally are employed per mole of magnesium in the halogenated product (i.e. supported catalyst component). Suitable acid halides include benzoyl chloride, phthaloyl dichloride, 2,3-naphthalenedicarboxylic acid dichloride, endo-5-norbornene-2,3-dicarboxylic acid dichloride, maleic acid dichloride, citraconic acid dichloride, and the like. A useful procedure for treatment of the halogentated product by acid halides is described in U.S. Pat. No. 6,825, 146.

After the supported catalyst component has been treated one or more times with additional tetravalent titanium halide, it is separated from the liquid reaction medium, and preferably washed with an inert hydrocarbon such as isopentane, isooctane, isohexane, hexane, pentane, heptane, or octane to remove unreacted titanium compounds or other imporities. The supported catalyst component can then be dried, or it may slurried in a hydrocarbon, especially a relatively heavy hydrocarbon such as mineral oil for further storage or use. If dried, the drying process may be by filtration, evaporation, heating or other methods known in the art.

Not wishing to be bound by any particular theory, it is believed that (1) further halogenation by contacting the previously formed supported catalyst component with a titanium halide compound, especially a solution thereof in a halohydrocarbon diluent, and/or (2) further washing the previously formed supported catalyst component with a halohydrocarbon at an elevated temperature (100° C. to 150° C.), results in desirable modification of the supported catalyst component, possibly by removal of certain inactive metal compounds that are soluble in the foregoing diluent. Accordingly, the supported catalyst component may be contacted with a halogenating agent, such as a mixture of a titanium halide and a halohydrocarbon diluent, such as $TiCl_4$ and chlorobenzene, one or more times prior to isolation or recovery. Correspondingly, the supported catalyst component may be washed at a temperature between 100° C. to 150° C. with a halohydrocarbon such as chlorobenzene or o-chlorotoluene one or more times prior to isolation or recovery.

The final supported catalyst component product suitably has a titanium content of from about 0.5 percent by weight to about 6.0 percent by weight, or from about 1.0 percent by weight to about 5.0 percent by weight. The weight ratio of titanium to magnesium in the solid supported catalyst component is suitably between about 1:3 and about 1:160, or between about 1:4 and about 1:50, or between about 1:6 and 1:30. The internal electron donor is present in the supported catalyst component in a molar ratio of internal electron donor to magnesium of from about 0.001:1 to about 10.0:1, or from about 0.01:1 to about 0.4:1. Weight percent is based on the total weight of the supported catalyst composition.

The internal electron donor material useful in this invention may be combined with additional internal electron donors such as ethers, esters, amines, imines, nitriles, phosphines, stibines, arsines, polyhydrocarbyl phosphonates, phosphinates, dialkylphthalates, phosphates or phosphine oxides, or alkyl aralkylphthalates, wherein the alkyl moiety contains from 1 to 10, preferably 2 to 6, carbon atoms and the aralkyl moiety contains from 7 to 10, preferably to 7 to 8, carbon atoms, or an alkyl ester of an aromatic monocarboxylic acid wherein the monocarboxylic acid moiety contains from 6 to 10 carbon atoms and the alkyl moiety contains from 1 to 6 carbon atoms. Such combination or incorporation of additional internal electron donors may occur in any of the steps employing the titanium compound.

Prepolymerization or encapsulation of the catalyst or supported catalyst component of this invention also may be carried out prior to being used in the polymerization or copolymerization of alpha olefins. A particularly useful prepolymerization procedure is described in U.S. Pat. No. 4,579,836, which is incorporated herein by reference.

Catalyst

The olefin polymerization catalyst (or "catalyst composition") includes the above-described supported catalyst component, a cocatalyst, and optionally a selectivity control agent (also know as an "SCA", "external donor", or "external electron donor"), and optionally an activity limiting agent (or "ALA").

Cocatalyst

The cocatalyst may be chosen from any of the known activators of olefin polymerization catalyst systems, but organoaluminum compounds are preferred. Such cocatalysts can be employed individually or in combinations thereof. Suitable organoaluminum cocatalysts have the formula $Al(R^{10})_f X^3_g H_h$ wherein: $X^3$ is F, Cl, Br, I, or $OR^{10}$, and $R^{10}$ are saturated hydrocarbon radicals containing from 1 to 14 carbon atoms, which radicals may be the same or different, and, if desired, substituted with any substituent which is inert under the reaction conditions employed during polymerization, f is 1 to 3, g is 0 to 2, h is 0 or 1, and f+g+h=3. Trialkylaluminum compounds are particularly preferred, particularly those wherein each of the alkyl groups contains from 1 to 6 carbon atoms, e.g., $Al(CH_3)_3$, $Al(C_2H_5)_3$, $Al(i-C_4H_9)_3$, and $Al(C_6H_{13})_3$.

SCA

Bounded by no particular theory, it is believed that provision of one or more SCA (selectivity control agent) in the catalyst composition can affect the following properties of the formant polymer: level of tacticity (i.e., xylene soluble material), molecular weight (i.e., melt flow), molecular weight distribution (MWD), melting point, and/or oligomer level. The SCA, also known as external donor or external electron donor, used in the invention is typically one of those known in the art. The SCAs known in the art include, but are not limited to, silicon compounds, esters of carboxylic acids, (especially diesters), monoethers, diethers (e.g., 1,3-dimethoxy propane or 2,2-diisobutyl-1,3 dimethoxy propane), and amines (e.g., tetramethylpiperidine).

Preferably, the silicon compounds employed as SCAs contain at least one silicon-oxygen-carbon linkage. Suitable silicon compounds include those having the formula $R^{11}_i SiY_j X^4_k$ wherein: $R^{11}$ is a hydrocarbon radical containing from 1 to 20 carbon atoms, Y is $—OR^{12}$ or $—OCOR^{12}$ wherein $R^{12}$ is a hydrocarbon radical containing from 1 to 20 carbon atoms, $X^4$ is hydrogen or halogen, i is an integer having a value of from 0 to 3, j is an integer having a value of from 1 to 4, k is an integer having a value of from 0 to 1, and preferably 0, and i+j+k=4. Preferably, $R^{11}$ and $R^{12}$ are alkyl, aryl or alkaryl ligands of $C_1$-$C_{10}$. Each $R^{11}$ and $R^{12}$ may be the same or different, and, if desired, substituted with any substituent which is inert under the reaction conditions employed during polymerization. Preferably, $R^{12}$ contains from 1 to 10 carbon atoms when it is aliphatic and may be sterically hindered or cycloaliphatic, and from 6 to 10 carbon atoms when it is aromatic.

Examples of $R^{11}$ include cyclopentyl, t-butyl, isopropyl, cyclohexyl or methyl cyclohexyl. Examples of $R^{12}$ include methyl, ethyl, butyl, isopropyl, phenyl, benzyl and t-butyl. Examples of $X^4$ are Cl and H. Preferred silicon SCAs are alkylalkoxysilanes such as diethyldiethoxysilane, diphenyl dimethoxy silane, diisobutyldimethoxysilane, cyclohexylmethyldimethoxysilane, n-propyltrimethoxysilane, or dicyclopentyldimethoxysilane.

Silicon compounds in which two or more silicon atoms are linked to each other by an oxygen atom, i.e., siloxanes or polysiloxanes, may also be employed, provided the requisite silicon-oxygen-carbon linkage is also present. Other preferred SCAs are esters of aromatic monocarboxylic or dicarboxylic acids, particularly alkyl esters, such as PEEB, DIBP, and methyl paratoluate.

The SCA is provided in a quantity sufficient to provide from about 0.01 mole to about 100 moles per mole of titanium in the procatalyst. It is preferred that the SCA is provided in a quantity sufficient to provide from about 0.5 mole to about 70 moles per mole of titanium in the procatalyst, with about 8 moles to about 50 moles being more preferred.

Nonlimiting examples of suitable silicon compounds for the SCA include those mentioned in U.S. Pat. No. 7,491,670, WO2009/029486, or WO2009/029487 and any combinations thereof.

The SCA can be a mixture of at least 2 silicon compounds (i.e., a mixed SCA, or mixed external electron donor, or "MEED"). A MEED may comprise two or more of any of the foregoing SCA compounds. A preferred mixture can be dicyclopentyldimethoxysilane and methylcyclohexyldimethoxysilane, dicyclopentyldimethoxysilane and tetraethoxysilane, or dicyclopentyldimethoxysilane and n-propyltriethoxysilane.

ALA

The catalyst composition may also includes an activity limiting agent (ALA). As used herein, an "activity limiting agent" ("ALA") is a material that reduces catalyst activity at elevated temperature (i.e., temperature greater than about 85° C.). An ALA inhibits or otherwise prevents polymerization reactor upset and ensures continuity of the polymerization process. Typically, the activity of Ziegler-Natta catalysts increases as the reactor temperature rises. Ziegler-Natta catalysts also typically maintain high activity near the melting point temperature of the polymer produced. The heat generated by the exothermic polymerization reaction may cause polymer particles to form agglomerates and may ultimately lead to disruption of continuity for the polymer production process. The ALA reduces catalyst activity at elevated temperature, thereby preventing reactor upset, reducing (or preventing) particle agglomeration, and ensuring continuity of the polymerization process.

The ALA may or may not be a component of the SCA and/or the MEED. The activity limiting agent may be a carboxylic acid ester, a diether, a poly(alkene glycol), a diol ester, and combinations thereof. The carboxylic acid ester can be an aliphatic or aromatic, mono- or poly-carboxylic acid ester. Nonlimiting examples of suitable monocarboxylic acid esters include ethyl and methyl benzoate, ethyl p-methoxybenzoate, methyl p-ethoxybenzoate, ethyl p-ethoxybenzoate, ethyl acrylate, methyl methacrylate, ethyl acetate, ethyl p-chlorobenzoate, hexyl p-aminobenzoate, isopropyl naphthenate, n-amyl toluate, ethyl cyclohexanoate and propyl pivalate.

Nonlimiting examples of suitable ALAs include those disclosed in WO2009085649, WO2009029487, WO2009029447, or WO2005030815, and combinations thereof.

The SCA and/or ALA can be added into the reactor separately. Alternatively, the SCA and the ALA can be mixed together in advance and then added to the catalyst composition and/or into the reactor as a mixture. In the mixture, more than one SCA or more than one ALA can be used. A preferred mixture is dicyclopentyldimethoxysilane and isopropyl myristate, dicyclopentyldimethoxysilane and poly(ethylene glycol) laurate, dicyclopentyldimethoxysilane and isopropyl myristate and poly(ethylene glycol) dioleate, methylcyclohexyldimethoxysilane and isopropyl myristate, n-propyltrimethoxysilane and isopropyl myristate, dimethyldimethoxysilane and methylcyclohexyldimethoxysilane and isopropyl myristate, dicyclopentyldimethoxysilane and n-propyltriethoxysilane and isopropyl myristate, and dicyclopentyldimethoxysilane and tetraethoxysilane and isopropyl myristate, and combinations thereof.

The catalyst composition may include any of the foregoing SCAs or MEEDs in combination with any of the foregoing activity limiting agents (or ALAs).

Preparation of the Catalyst or Catalyst Composition

The components of the olefin polymerization catalyst can be contacted by mixing in a suitable reactor outside the system in which olefin is to be polymerized and the catalyst thereby produced subsequently is introduced into the polymerization reactor. The premixed components may be dried after contact or left in the contact solvent. Alternatively, however, the catalyst components may be introduced separately into the polymerization reactor. As another alternative, two or more of the components may be mixed partially or completely with each other (e.g. premixing SCA and cocatalyst, or premixing the SCA and ALA) prior to being introduced into the polymerization reactor. Another alternative is to contact the supported catalyst component with an organoaluminum compound prior to reaction with the other catalyst components. A different alternative is to pre-polymerize a small amount of olefin with the catalyst components or put any of the components on a support (e.g., silica or a non-reactive polymer).

Polymerization

One or more olefin monomers can be introduced into a polymerization reactor to react with the catalyst and to form a polymer, or a fluidized bed of polymer particles. Nonlimiting examples of suitable olefin monomers include ethylene, propylene, $C_{4-20}$ α-olefins, such as 1-butene, 1-pentene, 1-hexene, 4-methyl-1-pentene, 1-heptene, 1-octene, 1-decene, 1-dodecene and the like; $C_{4-20}$ diolefins, such as 1,3-butadiene, 1,3-pentadiene, norbornadiene, 5-ethylidene-2-norbornene (ENB), and dicyclopentadiene; $C_{8-40}$ vinyl aromatic compounds including styrene, o-, m-, and p-methylstyrene, divinylbenzene, vinylbiphenyl, vinylnapthalene; and halogen-substituted $C_{8-40}$ vinyl aromatic compounds such as chlorostyrene and fluorostyrene.

As used herein, "polymerization conditions" are temperature and pressure parameters within a polymerization reactor suitable for promoting polymerization between the catalyst composition and an olefin to form the desired polymer. The polymerization process may be a gas phase, a slurry, or a bulk polymerization process, operating in one, or more than one, polymerization reactor. Accordingly, the polymerization reactor may be a gas phase polymerization reactor, a liquid-phase polymerization reactor, or a combination thereof.

It is understood that provision of hydrogen in the polymerization reactor is a component of the polymerization conditions. During polymerization, hydrogen is a chain transfer agent and affects the molecular weight (and correspondingly the melt flow rate) of the resultant polymer.

Polymerization may occur by way of gas phase polymerization. As used herein, "gas phase polymerization" is the passage of an ascending fluidizing medium, the fluidizing medium containing one or more monomers, in the presence of a catalyst through a fluidized bed of polymer particles maintained in a fluidized state by the fluidizing medium. "Fluidization," "fluidized," or "fluidizing" is a gas-solid contacting process in which a bed of finely divided polymer particles is lifted and agitated by a rising stream of gas. Fluidization occurs in a bed of particulates when an upward flow of fluid through the interstices of the bed of particles attains a pressure differential and frictional resistance increment exceeding particulate weight. Thus, a "fluidized bed" is a plurality of polymer particles suspended in a fluidized state by a stream of a fluidizing medium. A "fluidizing medium" is one or more olefin gases, optionally a carrier gas (such as $H_2$ or $N_2$) and optionally a liquid (such as a hydrocarbon) which ascends through the gas-phase reactor.

A typical gas-phase polymerization reactor (or gas phase reactor) includes a vessel (i.e., the reactor), the fluidized bed, a distribution plate, inlet and outlet piping, a compressor, a cycle gas cooler or heat exchanger, and a product discharge system. The vessel includes a reaction zone and a velocity reduction zone, each of which is located above the distribution plate. The bed is located in the reaction zone. In an embodiment, the fluidizing medium includes propylene gas and at least one other gas such as an olefin and/or a carrier gas such as hydrogen or nitrogen.

Contacting of the catalyst and the olefin occurs by way of feeding the catalyst composition into a polymerization reactor and introducing the olefin into the polymerization reactor. The cocatalyst can be mixed with the supported catalyst component (pre-mix) prior to the introduction of the supported catalyst component into the polymerization reactor. The cocatalyst may also be added to the polymerization reactor independently of the supported catalyst component. The independent introduction of the cocatalyst into the polymerization reactor can occur simultaneously, or substantially simultaneously, with the supported catalyst component feed.

The polymerization process may include a pre-polymerization step. Pre-polymerization includes contacting a small amount of the olefin with the procatalyst composition after the supported catalyst component has been contacted with the co-catalyst and the SCA and/or the activity limiting agent. Then, the resulting preactivated catalyst stream is introduced into the polymerization reaction zone and contacted with the remainder of the olefin monomer to be polymerized, and optionally one or more of the SCA components and/or activity limiting agent components. Pre-polymerization results in the supported catalyst component being combined with the cocatalyst and the SCA and/or the activity limiting agent, the combination being dispersed in a matrix of the formant polymer. Optionally, additional quantities of the SCA and/or the activity limiting agent may be added.

The polymerization process may include a pre-activation step. Pre-activation includes contacting the supported catalyst component with the co-catalyst and the SCA and/or the activity limiting agent. The resulting preactivated catalyst stream is subsequently introduced into the polymerization reaction zone and contacted with the olefin monomer to be polymerized, and optionally one or more of the SCA components. Pre-activation results in the supported catalyst component being combined with the cocatalyst and the SCA and/or the activity limiting agent. Optionally, additional quantities of the SCA and/or the activity limiting agent may be added.

The process may include mixing the SCA (and optionally the activity limiting agent) with the supported catalyst component. The SCA can be complexed with the cocatalyst and mixed with the supported catalyst component (pre-mix) prior to contact between the catalyst composition and the olefin. The SCA and/or the activity limiting agent can be added independently to the polymerization reactor. Preferred SCAs include dicyclopentyldimethoxysilane or n-propyltrimethoxysilane.

A preferred catalyst composition includes an SCA such as dicyclopentyldimethoxysilane and/or n-propyltrimethoxysilane and/or methylcyclohexyldimethoxysilane, and an activity limiting agent such as isopropyl myristate.

The olefin may be propylene wherein the process includes forming a propylene-based polymer having a melt flow rate (MFR) from about 0.01 g/10 min to about 800 g/10 min, or from about 0.1 g/10 min to about 200 g/10 min, or from about 0.5 g/10 min to about 150 g/10 min. Further, the propylene-based polymer is a polypropylene homopolymer.

The olefin may be propylene wherein the process includes forming a propylene-based polymer having a xylene solubles content from about 0.5% to about 10%, or from about 1% to about 8%, or from about 1% to about 4%. Further, the propylene-based polymer is a polypropylene homopolymer.

The present disclosure provides another process for producing an olefin-based polymer. The olefin may be propylene and a mixture of at least one other suitable olefin comonomer wherein the process includes forming a propylene-based interpolymer. The preferred comonomer is ethylene and/or 1-butene and the formant interpolymer has a melt flow rate (MFR) from about 0.01 g/10 min to about 200 g/10 min, or from about 0.1 g/10 min to about 100 g/10 min, or from about 0.5 g/10 min to about 70 g/10 min. Further, the preferred propylene-based interpolymer is a random copolymer.

The olefin may be propylene and a mixture of at least one other suitable olefin comonomer wherein the process includes forming a propylene-based interpolymer. The preferred comonomer is ethylene and/or 1-butene and the formant interpolymer has a xylene solubles content from about 0.5% to about 40%, or from about 1% to about 30%, or from about 1% to about 20%. Further, the preferred propylene-based interpolymer is a random copolymer.

The olefin may be propylene and a mixture of at least one other suitable olefin comonomer wherein the process includes forming a propylene-based interpolymer. The preferred comonomer is ethylene and/or 1-butene and the formant interpolymer has a weight percent comonomer content relative to propylene of from about 0.001% to about 20%, or from about 0.01% to about 15%, or from about 0.1% to about 10%. Further, the preferred propylene-based interpolymer is a random copolymer.

The present disclosure provides another process for producing an olefin-based polymer. A process for producing an olefin-based polymer is provided which includes contacting propylene with a catalyst composition comprising a dicarbonate to form a propylene-based polymer. The contact between the propylene and the catalyst composition occurs in a first polymerization reaction under polymerization conditions. The process further includes contacting ethylene and optionally at least one other olefin in the presence of the propylene-based polymer. The contact between the ethylene, the olefin(s), and the propylene-based polymer occurs in a second polymerization reactor under polymerization conditions and forms a propylene impact copolymer.

The first reactor and the second reactor may operate in series whereby the effluent of the first reactor (i.e., the propylene-based polymer) is charged to the second reactor. Additional olefin monomer is added to the second polymerization reactor to continue polymerization. Additional catalyst composition (and/or any combination of individual catalyst components—i.e., supported catalyst component, cocatalyst, EED or MEED, ALA) may be added to the second polymerization reactor. The additional catalyst composition/components added to the second reactor may be the same or different than the catalyst composition/components introduced in the first reactor.

The propylene-based polymer produced in the first reactor is a propylene homopolymer. The propylene homopolymer is charged to the second reactor where ethylene and propylene are contacted with each other in the presence of the propylene homopolymer. This forms a propylene impact copolymer having a propylene homopolymer continuous (or matrix) phase and a discontinuous phase (or rubber phase) selected from a propylene-based copolymer (i.e., a propylene/ethylene copolymer) or an ethylene-based copolymer (i.e., an ethylene/propylene copolymer). The discontinuous phase is dispersed in the continuous phase.

The propylene impact copolymer may have an Fc value from about 1 wt % to about 50 wt %, or from about 10 wt % to about 40 wt %, or from about 20 wt % to about 30 wt %. As used herein, "fraction copolymer" ("Fc") is the weight percent of the discontinuous phase present in the heterophasic copolymer. The Fc value is based on the total weight of the propylene impact copolymer.

The propylene impact copolymer may have an Ec value from about 1 wt % to about 100 wt %, or from about 20 wt % to about 90 wt %, or from about 30 wt % to about 80 wt %, or from about 40 wt % about 60 wt %. As used herein, "ethylene content" ("Ec") is the weight percent of ethylene present in the discontinuous phase of the propylene impact copolymer. The Ec value is based on the total weight of the discontinuous (or rubber) phase.

Test Methods

Polydispersity Index (PDI) is measured by an AR-G2 rheometer which is a stress control dynamic spectrometer manufactured by TA Instruments using a method according to Zeichner G. R., Patel P. D. (1981) "A comprehensive Study of Polypropylene Melt Rheology" Proc. of the 2nd World Congress of Chemical Eng., Montreal, Canada. An ETC oven is used to control the temperature at 180° C.±0.1° C. Plant nitrogen purged inside the oven to keep sample from degradation by oxygen and moisture. A pair of 25 mm in diameter cone and plate sample holder is used. Samples are compress molded into 50 mm×100 mm×2 mm plaque. Samples are cut into 19 mm square and loaded on the center of the bottom plate. The geometries of upper cone is (1) Cone angle: 5:42: 20 (deg:min:sec); (2) Diameter: 25 mm; (3) Truncation gap: 149 micron. The geometry of the bottom plate is 25 mm cylinder. Testing procedure:
- (i) The cone & plate sample holder are heated in the ETC oven at 180° C. for 2 hours. Then the gap is zeroed under blanket of nitrogen gas.
- (ii) Cone is raised to 2.5 mm and sample loaded unto the top of the bottom plate.
- (iii) Start timing for 2 minutes.
- (iv) The upper cone is immediately lowered to slightly rest on top of the sample by observing the normal force.
- (v) After two minutes the sample is squeezed down to 165 micron gap by lower the upper cone.
- (vi) The normal force is observed when the normal force down to <0.05 Newton the excess sample is removed from the edge of the cone and plate sample holder by a spatula.
- (vii) The upper cone is lowered again to the truncation gap which is 149 micron.
- (viii) An Oscillatory Frequency Sweep test is performed under these conditions:
  Test delayed at 180° C. for 5 minutes.
  Frequencies: 628.3 r/s to 0.1 r/s.
  Data acquisition rate: 5 point/decade.
  Strain: 10%
- (ix) When the test is completed the crossover modulus (Gc) is detected by the Rheology Advantage Data Analysis program furnished by TA Instruments.
- (x) PDI=100,000÷Gc (in Pa units).

Melt flow rate (MFR) or "Melt flow" is measured in accordance with ASTM D 1238-01 test method at 230° C. with a 2.16 kg weight for propylene-based polymers.

Xylene Solubles (XS) is measured according to the following procedure. A total of 0.4 g of polymer is dissolved in 20 ml of xylenes with stirring at 130° C. for 30 minutes. The solution is then cooled to 25° C., and after 30 minutes the insoluble polymer fraction is filtered off. The resulting filtrate is analyzed by Flow Injection Polymer Analysis using a Viscotek ViscoGEL H-100-3078 column with THF mobile phase flowing at 1.0 ml/min. The column is coupled to a Viscotek Model 302 Triple Detector Array, with light scattering, viscometer and refractometer detectors operating at 45° C. Instrument calibration was maintained with Viscotek Poly-CAL™ polystyrene standards.

Final melting point, $T_{MF}$ or ("TMF"), is the temperature to melt the most perfect crystal in the sample and is regarded as a measure for isotacticity and inherent polymer crystallizability. The test is conducted using a TA Q100 Differential Scanning Calorimeter. A sample is heated from 0° C. to 240° C. at a rate of 80° C./min, cooled at the same rate to 0° C., then heated again at the same rate up to 150° C., held at 150° C. for 5 minutes and the heated from 150° C. to 180° C. at 1.25° C./min. The $T_{MF}$ is determined from this last cycle by calculating the onset of the baseline at the end of the heating curve.

Testing Procedure for TMF:
- (1) Calibrate instrument with high purity indium as standard.
- (2) Purge the instrument head/cell with a constant 50 ml/min flow rate of nitrogen constantly.
- (3) Sample preparation: Compression mold 1.5 g of powder sample using a 30-G302H-18-CX Wabash Compression Molder (30 ton): (a) heat mixture at 230° C. for 2 minutes at contact; (b) compress the sample at the same temperature with 20 ton pressure for 1 minute; (c) cool the sample to 45° F. and hold for 2 minutes with 20 ton pressure; (d) cut the plaque into 4 of about the same size, stack them together, and repeat steps (a)-(c) in order to homogenize sample.
- (4) Weigh a piece of sample (preferably between 5 to 8 mg) from the sample plaque and seal it in a standard aluminum sample pan. Place the sealed pan containing the sample on the sample side of the instrument head/cell and place an empty sealed pan in the reference side. If using the auto sampler, weigh out several different sample specimens and set up the machine for a sequence.
- (5) Measurements:
  - (i) Data storage: off
  - (ii) Ramp 80.00° C./min to 240.00° C.
  - (iii) Isothermal for 1.00 min (iv) Ramp 80.00° C./min to 0.00° C.
(v) Isothermal for 1.00 min
(vi) Ramp 80.00° C./min to 150.00° C.
(vii) Isothermal for 5.00 min
(viii) Data storage: on
(ix) Ramp 1.25° C./min to 180.00° C.
(x) End of method
(6) Calculation: $T_{MF}$ is determined by the interception of two lines. Draw one line from the base-line of high temperature. Draw another line from through the deflection of the curve close to the end of the curve at high temperature side.

The following Examples are meant to help illustrate the present invention but are not intended to limit the scope of the invention as defined by the claims.

EXAMPLES

General procedure for the preparation of dimethyl naphthalene-1,8-diyl dicarbonate (ID-1), diethyl naphthalene-1,8-diyl dicarbonate (ID-2), dipropyl naphthalene-1,8-diyl dicarbonate (ID-3), and dibutyl naphthalene-1,8-diyl dicarbonate (ID-4): To a round-bottom flask is charged naphthalene-1,8-diol (4.0 g, 25 mmol), pyridine (4.0 g, 50 mmol), and anhydrous methylene chloride (50 ml). The flask is immersed in an ice-water bath, and the appropriate chloroformate (50 mmol) is added dropwise. The mixture was raised to room temperature and stirred overnight. The mixture is diluted with additional methylene chloride and after filtration the combined organics are washed sequentially with water, saturated $NH_4Cl$ or 1N HCl solution (aqueous), water, saturated sodium bicarbonate (aqueous), and brine, and then dried over magnesium sulfate. After filtration, the filtrate is concentrated, and the residue is purified by recrystallization from methanol or ethanol, or by flash column chromatography on silica gel.

Dimethyl naphthalene-1,8-diyl dicarbonate (ID-1): Prepared using methyl chloroformate; purified by recrystallization from methanol to yield the product as brown crystals (58.0%). $^1$H NMR (400 MHz, $CDCl_3$, ppm) δ 7.80 (dd, 2H, J=1.2, 8.4 Hz), 7.48 (dd, 2H, J=7.6, 8.4 Hz), 7.26 (d, 2H, J=1.2, 7.6 Hz), 3.95 (s, 6H).

Diethyl naphthalene-1,8-diyl dicarbonate (ID-2): Prepared using ethyl chloroformate; purified by recrystallization from ethanol to yield the product as a lightly colored solid (60.5%). $^1$H NMR (500 MHz, $CDCl_3$, ppm) δ 7.79 (d, 2H, J=8.0 Hz), 7.47 (dd, 2H, J=7.5, 8.0 Hz), 7.26 (d, 2H, J=7.5 Hz), 4.36 (q, 4H, J=7.5 Hz), 1.43 (t, 6H, J=7.5 Hz).

Dipropyl naphthalene-1,8-diyl dicarbonate (ID-3): Prepared using propyl chloroformate; purified by flash column chromatography on silica gel to yield the product as a white solid (90%); $^1$H NMR (500 MHz, $CDCl_3$) δ 7.80 (dd, J=0.5, 8.0 Hz, 2H), 7.48 (dd, J=7.5, 8.0 Hz, 2H), 7.27 (dd, J=0.5, 7.5, 2H), 4.26 (t, J=6.8 Hz, 4H), 1.82 (hex, J=7.3 Hz, 4H), 1.04 (t, J=7.5 Hz, 6H).

Dibutyl naphthalene-1,8-diyl dicarbonate (ID-4): Prepared using butyl chloroformate; purified by flash column chromatography on silica gel to yield the product as a white solid (85%); $^1$H NMR (500 MHz, $CDCl_3$) δ 7.80 (d, J=9.0 Hz, 2H), 7.48 (t, J=8.0 Hz, 2H), 7.27 (d, J=7.5, 2H), 4.31 (t, J=6.8 Hz, 4H), 1.82 (pent, J=5.8 Hz, 4H), 1.82 (hex, J=7.5 Hz, 4H), 1.04 (t, J=7.5 Hz, 6H).

Preparation of diisobutyl naphthalene-1,8-diyl dicarbonate (ID-5): To a round-bottom flask is charged naphthalene-1,8-diol (4.0 g, 25 mmol), and anhydrous DMF (50 ml). The flask is immersed in an ice-water bath, and 60% sodium hydride in mineral oil (2.4 g, 60 mmol) is added in portions. The mixture is stirred for an hour. Isobutyl chloroformate (8.2 g, 60 mmol) is added dropwise. After gradually warming to room temperature, the mixture is stirred overnight. The mixture is poured into ice-cold water and extracted with ether three times. The combined ether extracts are washed with water, then brine, and then dried over magnesium sulfate. After filtration, the filtrate is concentrated, and the residue is purified by flash column chromatography on silica gel to yield 2.8 g (31%) of the product as a light-grey solid. $^1$H NMR (400 MHz, $CDCl_3$, ppm) δ 7.79 (dd, 2H, J=1.2, 8.0 Hz), 7.47 (dd, 2H, J=7.6, 8.0 Hz), 7.26 (dd, 2H, J=1.2, 7.6 Hz), 4.07 (d, 4H, J=6.8 Hz), 2.07 (m, 2H), 1.00 (d, 12 H, J=6.8 Hz).

Preparation of biphenyl-2,2'-diyl diethyl dicarbonate (ID-6): To a round-bottom flask is charged biphenyl-2,2'-diol (7.45 g, 40 mmol) and pyridine (50 mL). The flask is immersed in an ice-water bath and ethyl chloroformate (9.48 mL, 100 mmol) is added dropwise. After gradually warming to room temperature, the mixture is stirred overnight. The volatiles are removed in vacuo, and the residue is suspended in 100 mL of ethyl acetate. After filtration, the filtrate is concentrated and purified by flash chromatography. The product is obtained as a colorless oil. Yield: 5.0 g; $^1$H NMR (500 MHz, $CDCl_3$, ppm) δ 7.23-7.44 (m, 8H), 4.13 (q, 4H), 1.19 (t, 6H).

Structures of the internal donors which were obtained commercially (diisobutyl phthalate and diethyl carbonate), or prepared as described herein, are shown in Table 1.

TABLE 1

Structure of the Internal Donors used in Examples:

| Chemical Name | Donor Identity | Structure |
|---|---|---|
| diisobutyl phthalate (CAS # 84-69-5) | DIBP (comparative) | 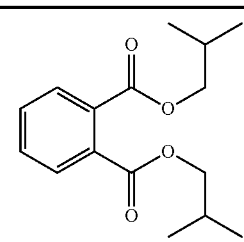 |
| diethyl carbonate (CAS # 105-58-8) | DEC (comparative) | 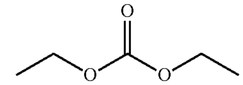 |

TABLE 1-continued

Structure of the Internal Donors used in Examples:

| Chemical Name | Donor Identity | Structure |
| --- | --- | --- |
| dimethyl naphthalene-1,8-diyl dicarbonate | ID-1 | 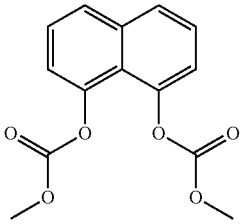 [SMILES: COC(=O)Oc1cccc2cccc(OC(=O)OC)c12] |
| diethyl naphthalene-1,8-diyl dicarbonate | ID-2 | 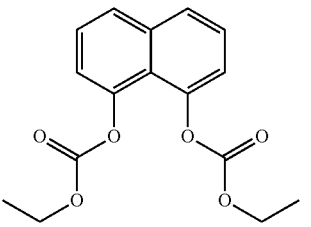 [SMILES: CCOC(=O)Oc1cccc2cccc(OC(=O)OCC)c12] |
| dipropyl naphthalene-1,8-diyl dicarbonate | ID-3 | 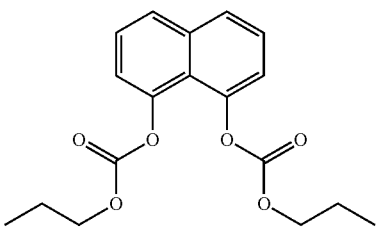 [SMILES: CCCOC(=O)Oc1cccc2cccc(OC(=O)OCCC)c12] |
| dibutyl naphthalene-1,8-diyl dicarbonate | ID-4 | 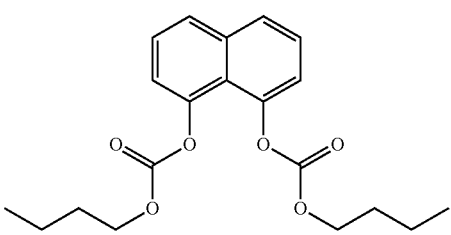 [SMILES: CCCCOC(=O)Oc1cccc2cccc(OC(=O)OCCCC)c12] |
| diisobutyl naphthalene-1,8-diyl dicarbonate | ID-5 | 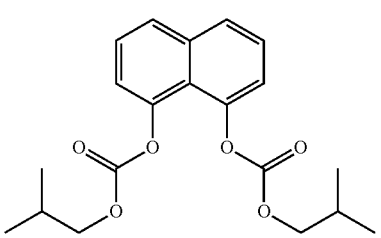 [SMILES: CC(C)COC(=O)Oc1cccc2cccc(OC(=O)OCC(C)C)c12] |
| biphenyl-2,21-diyl diethyl dicarbonate | ID-6 | 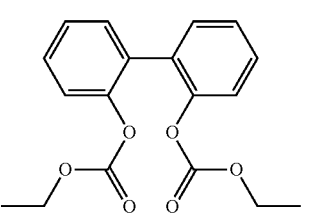 [SMILES: CCOC(=O)Oc1ccccc1-c1ccccc1OC(=O)OCC] |

Preparation of Supported Catalyst Components

Under nitrogen, 3.0 g of MagTi (mixed magnesium/titanium halide alcoholate; CAS # 173994-66-6, see U.S. Pat. No. 5,077,357), the amount of internal electron donor indicated in Table 2 below, and 60 mL of a 50/50 (vol/vol) mixture of titanium tetrachloride and chlorobenzene is charged to a vessel equipped with an integral filter. After heating to 115° C. for 60 minutes with stirring, the mixture is filtered. The solids are treated with an additional 60 mL of fresh 50/50 (vol/vol) mixed titanium tetrachloride/chlorobenzene, and optionally (as indicated in table 2 below), a second charge of internal electron donor, at 115° C. for 30 minutes with stirring. The mixture is filtered. The solids are again treated with 60 mL of fresh 50/50 (vol/vol) mixed titanium tetrachloride/chlorobenzene at 115° C. for 30 minutes with stirring. The mixture is filtered. At ambient temperature, the solids are washed three times with 70 mL of isooctane, then dried under a stream of nitrogen. The solid catalyst components are collected as powders and a portion is mixed with mineral oil to produce a 5.4 wt % slurry. The identity of internal electron donor used, their amounts, and timing of addition are detailed below (Table 2).

TABLE 2

Amounts of Internal Donors Used for Supported Catalyst Components

| Solid Catalyst Designation | Internal Electron Donor | mmol donor (1st hot addition) | mmol donor (2nd hot addition) |
|---|---|---|---|
| Comp 1a | DIBP | 2.42 | 0.0 |
| Comp 1b | DIBP | 2.42 | 0.0 |
| Comp 2 | DEC | 2.42 | 0.0 |
| Cat 1 | ID-1 | 2.42 | 0.0 |
| Cat 2-1 | ID-2 | 2.42 | 0.0 |
| Cat 2-2 | ID-2 | 1.57 | 1.57 |
| Cat 3 | ID-3 | 2.42 | 0.0 |
| Cat 4 | ID-4 | 2.42 | 0.0 |
| Cat 5 | ID-5 | 2.42 | 0.0 |
| Cat 6 | ID-6 | 2.42 | 0.0 |

Generation of Active Polymerization Catalyst

In an inert atmosphere glovebox the active catalyst mixture is prepared by premixing the quantities indicated in Tables 3-5 of external donor (if present), triethylaluminum (as a 0.28 M solution), supported catalyst component (as a 5.4% mineral oil slurry), and 5-10 mL isooctane diluent (optional) for 20 minutes. After preparation, and without exposure to air, the active catalyst mixture is injected into the polymerization reactor as described below. Batch Reactor Propylene Polymerization (Homopolymer):

Polymerizations are conducted in a stirred, 3.8 L stainless steel autoclave. Temperature control is maintained by heating or cooling an integrated reactor jacket using circulated water. The top of the reactor is unbolted after each run so that the contents can be emptied after venting the volatiles. All chemicals used for polymerization or catalyst preparation are run through purification columns to remove impurities. Propylene and solvents are passed through 2 columns, the first containing alumina, the second containing a purifying reactant (Q5™ available from Engelhard Corporation). Nitrogen and hydrogen gases are passed through a single column containing Q5™ reactant.

After attaching the reactor head to the body, the reactor is purged with nitrogen while being heated to 140° C. and then while cooling to approximately 30° C. The reactor is then filled with a solution of diethylaluminum chloride in isooctane (1 wt %) and agitated for 15 minutes. This scavenging solution is then flushed to a recovery tank and the reactor is filled with ~1375 g of propylene. The appropriate amount of hydrogen is added using a mass flow meter (see Tables 3-5) and the reactor is brought to 62° C. The active catalyst mixture is injected as a slurry in oil or light hydrocarbon and the injector is flushed with isooctane three times to ensure complete delivery. After injection of catalyst, the reactor temperature is ramped to 67° C. over 5 minutes, or maintained at 67° C. via cooling in the case of large exotherms. After a run time of 1 hour, the reactor is cooled to ambient temperature, vented, and the contents are emptied. Polymer weights are measured after drying overnight or to constant weight in a ventilated fume hood.

TABLE 3

Polymerization Results at 0.14 mol % ($H_2/C_3$)

| Example # | Solid Catalyst Designation | Internal Donor | External Donor | Yield PP (g) | Melt Flow (g/10 min) | XS | TMF (° C.) | PDI | Eff (kg PP/g cat) |
|---|---|---|---|---|---|---|---|---|---|
| 1c | Comp 1a* | DIBP | NPTMS | 272 | 5.6 | 2.6 | 170.2 | 3.86 | 25 |
| 2 | Cat 2-1 | ID-2 | NPTMS | 309 | 2.0 | 1.6 | 172.8 | 3.58 | 29 |
| 3 | Cat 2-2 | ID-2 | NPTMS | 228 | 3.2 | 1.5 | 172.7 | 3.58 | 21 |
| 4c | Comp 1a* | DIBP | DCPDMS | 356 | 2.9 | 3.1 | 171.7 | 4.46 | 33 |
| 5 | Cat 2-1 | ID-2 | DCPDMS | 363 | 2.3 | 1.7 | 172.7 | 3.84 | 34 |
| 6 | Cat 2-2 | ID-2 | DCPDMS | 299 | 2.5 | 1.6 | 172.8 | 3.86 | 28 |
| 7 | Cat 2-2 | ID-2 | none | 329 | 4.1 | 3.1 | 172.0 | 4.19 | 31 |

*= comparative; not an example of the invention
Conditions: 200 mg catalyst slurry; 0.15 mmol external donor (if present); 1.5 mmol Al Analysis of the data in Table 3 reveals the following:
A. The TMF of polymer from catalysts employing inventive donor (ID-2) is higher than when using the comparative catalyst.
B. When an external donor is used, the XS of polymer from catalysts employing inventive donor (ID-2) is lower than when using the comparative catalyst.
C. Even in the absence of external donor, the XS of polymer from the catalyst employing inventive donor (ID-2) is equivalent to polymer made using the comparative catalyst in combination with an external donor.
D. The PDI of polymer from catalysts employing inventive donor (ID-2) is narrower than when using the comparative catalyst, and is relatively insensitive to change when varied external donors are employed
E. Efficiency of the inventive catalysts is strong (>20 kg PP/g catalyst).

TABLE 4

Polymerization Results at 0.41 mol % ($H_2/C_3$)

| Example # | Solid Catalyst Designation | Internal Donor | External Donor | Yield PP (g) | Melt Flow (g/10 min) | XS | TMF (° C.) | PDI | Eff (kg PP/g cat) |
|---|---|---|---|---|---|---|---|---|---|
| 8c | Comp 1b* | DIBP | NPTMS | 261 | 28.1 | 2.8 | 169.9 | 4.11 | 24 |
| 9c | Comp 2* | DEC | NPTMS | 180 | 48.9 | 10.9 | — | — | 17 |
| 10 | Cat 1 | ID-1 | NPTMS | 160 | 41.4 | 2.2 | 171.4 | 3.86 | 15 |
| 11 | Cat 2-1 | ID-2 | NPTMS | 338 | 13.0 | 1.7 | 172.2 | 3.64 | 32 |
| 12 | Cat 2-2 | ID-2 | NPTMS | 254 | 20.8 | 1.4 | 172.1 | 3.61 | 24 |
| 13 | Cat 3 | ID-3 | NPTMS | 267 | 12.9 | 1.4 | 171.8 | 3.56 | 25 |
| 14 | Cat 4 | ID-4 | NPTMS | 308 | 9.8 | 1.7 | 171.8 | 3.59 | 29 |
| 15 | Cat 5 | ID-5 | NPTMS | 181 | 23.0 | 2.5 | 171.0 | 4.23 | 17 |
| 16c | Comp 1b* | DIBP | DCPDMS | 308 | 10.0 | 3.2 | 171.5 | 4.81 | 29 |
| 17c | Comp 2* | DEC | DCPDMS | 367 | 35.0 | 11.4 | — | — | 34 |
| 18 | Cat 1 | ID-1 | DCPDMS | 193 | 37.4 | 2.0 | 171.4 | 4.23 | 18 |
| 19 | Cat 2-1 | ID-2 | DCPDMS | 398 | 10.4 | 1.6 | 172.4 | 3.99 | 37 |
| 20 | Cat 2-2 | ID-2 | DCPDMS | 350 | 15.4 | 1.7 | 172.2 | 3.97 | 33 |
| 21 | Cat 3 | ID-3 | DCPDMS | 419 | 7.3 | 2.1 | 171.8 | 4.31 | 39 |
| 22 | Cat 4 | ID-4 | DCPDMS | 414 | 6.5 | 2.3 | 172.0 | 4.11 | 39 |
| 23 | Cat 5 | ID-5 | DCPDMS | 278 | 10.5 | 3.9 | 171.3 | 5.55 | 26 |
| 24 | Cat 6 | ID-6 | DCPDMS | 155 | 37.4 | 5.3 | 169.9 | 4.98 | 15 |

*= comparative; not an example of the invention
"—" = not determined
Conditions: 200 mg catalyst slurry; 0.15 mmol external donor; 1.5 mmol Al Analysis of the data in Table 4 reveals the following:
  A. The XS of polymer from catalysts employing any of the inventive dicarbonate donors is much lower than when using the monocarbonate comparative catalyst (Comp 2).
  B. The TMF of polymer from catalysts employing inventive donors (ID-2, ID-3, or ID-4) is higher than when using the comparative catalyst (Comp 1b).
  C. The XS of polymer from catalysts employing inventive donors (ID-1, ID-2, ID-3, or ID-4) is lower than when using the comparative catalyst (Comp 1b or Comp 2).
  D. The PDI of polymer from catalysts employing inventive donors (ID-1, ID-2, ID-3, or ID-4) is narrower than when using the comparative catalyst (Comp 1b), and is relatively insensitive to change when varied external donors are employed.
  E. The PDI of polymer from the catalyst employing inventive donor (ID-5) is broader than when using the comparative catalyst (Comp 1b).
  F. The MF and PDI of polymer from the catalyst employing inventive donor (ID-6) is higher than when using the comparative catalyst (Comp 1b or Comp 2).
  G. The MF of inventive catalysts where $R_1$ has >2 unbranched carbon atoms (ID-3, ID-4) is lower than those examples where $R_1$ has <3 carbon atoms (ID-1, ID-2).
  H. Efficiency of the inventive catalysts is strong (>15 kg PP/g catalyst).

TABLE 5

Polymerization Results at 0.82 mol % ($H_2/C_3$)

| Example # | Solid Catalyst Designation | Internal Donor | External Donor | Yield PP (g) | Melt Flow (g/10 min) | XS | TMF (° C.) | PDI | Eff (kg PP/g cat) |
|---|---|---|---|---|---|---|---|---|---|
| 25c | Comp 1a* | DIBP | NPTMS | 283 | 53.2 | 3.0 | 169.4 | 4.22 | 27 |
| 26 | Cat 2a-1 | ID-2 | NPTMS | 250 | 107.2 | 1.4 | 171.1 | hmf | 23 |
| 27 | Cat 2-2 | ID-2 | NPTMS | 215 | 94.8 | 1.2 | 171.3 | hmf | 20 |
| 28c | Comp 1a* | DIBP | DCPDMS | 448 | 25.6 | 3.2 | 171.2 | 5.21 | 42 |
| 29 | Cat 1 | ID-1 | DCPDMS | 172 | 119.3 | 2.1 | — | — | 16 |
| 30 | Cat 2-1 | ID-2 | DCPDMS | 367 | 47.1 | 2.2 | 171.4 | 4.05 | 34 |
| 31 | Cat 2-2 | ID-2 | DCPDMS | 270 | 54.6 | 1.7 | 171.3 | 4.02 | 25 |
| 32 | Cat 3 | ID-3 | DCPDMS | 478 | 26.1 | 2.6 | 171.1 | 4.26 | 44 |
| 33 | Cat 4 | ID-4 | DCPDMS | 452 | 21.1 | 2.1 | 171.6 | 4.12 | 42 |
| 34 | Cat 5 | ID-5 | DCPDMS | 189 | 35.2 | 3.2 | — | — | 18 |
| 35 | Cat 2-2 | ID-2 | none | 403 | 98.9 | 3.3 | 170.6 | hmf | 38 |

*= comparative; not an example of the invention
"—" = not determined
hmf = polymer is "high melt flow" and yields a PDI measurement which must be extrapolated
Conditions: 200 mg catalyst slurry; 0.15 mmol external donor (if present); 1.5 mmol Al Analysis of the data in Table 5 reveals the following:
A. The TMF of polymer from catalysts employing inventive donor (ID-2) is higher than when using the comparative catalyst.
B. The XS of polymer from catalysts employing inventive donors (ID-2, ID-3, and ID-4) is lower than when using the comparative catalyst.
C. The PDI of polymer from catalysts employing inventive donors (ID-2, ID-3, and ID-4) is narrower than when using the comparative catalyst.
D. The MF of polymer from catalysts employing inventive donors (ID-1, ID-2, ID-3, and ID-5) is higher than when using the comparative catalyst.
E. The MF of inventive catalysts where $R_1$ has >2 carbon atoms (ID-3, ID-4, ID-5) is lower than those examples where $R_1$ has <3 carbon atoms (ID-1, ID-2).
F. The efficiency of inventive catalysts where $R_1$ has >2 unbranched carbon atoms (ID-3, ID-4) is higher than those examples where $R_1$ has <3 carbon atoms (ID-1, ID-2).
G. The MF increase of polymer from catalysts employing inventive donors (ID-1 or ID-2) is substantial relative to when the comparative catalyst is used. Therefore, higher MF polymer resin can be made without cracking.
H. Efficiency of the inventive catalysts is strong (>15 kg PP/g catalyst).

What is claimed is:

1. A solid, hydrocarbon-insoluble catalyst component useful in polymerizing olefins, said catalyst component containing magnesium, titanium, and halogen, and further containing an internal electron donor having a structure:

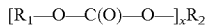

wherein $R_1$ is independently at each occurrence, an aliphatic or aromatic hydrocarbon, or substituted hydrocarbon group containing from 1 to 20 carbon atoms; x is 2-4; and $R_2$ is an aliphatic or aromatic hydrocarbon, or substituted hydrocarbon group containing from 1 to 20 carbon atoms, provided that there are from 3 to 4 atoms in the shortest chain connecting a first $R_1$—O—C(O)—O— group and a second $R_1$—O—C(O)—O— group.

2. The catalyst component of claim 1 where x=2.

3. The catalyst component of claim 1 where each $R_1$ is an aliphatic hydrocarbon.

4. The catalyst component of claim 1 where each $R_1$ is an aromatic hydrocarbon.

5. The catalyst component of claim 1 where $R_2$ is a 1,8-disubstituted naphthylene moiety.

6. The catalyst component of claim 1 where $R_2$ is a 2,2'-disubstituted biphenyl moiety.

7. The catalyst component of claim 1 where $R_2$ is a straight or branched alkyl moiety, provided that there are from 3 to 4 atoms in the shortest chain connecting a first $R_1$—O—C(O)—O— group and a second $R_1$—O—C(O)—O— group.

8. The catalyst component of claims 5 where each $R_1$ is an aliphatic hydrocarbon.

9. The catalyst component of claims 5 where each $R_1$ is methyl, ethyl, propyl, butyl, or isobutyl.

10. The catalyst component of claim 1 where the internal electron donor comprises one of the following compounds: dimethyl naphthalene-1,8-diyl dicarbonate; diethyl naphthalene-1,8-diyl dicarbonate; dipropyl naphthalene-1,8-diyl dicarbonate; dibutyl naphthalene-1,8-diyl dicarbonate; diisobutyl naphthalene-1,8-diyl dicarbonate; or biphenyl-2,2'-diyl diethyl dicarbonate.

11. The catalyst component of claim 1 where the internal electron donor comprises one of the following compounds: diethyl naphthalene-1,8-diyl dicarbonate; dipropyl naphthalene-1,8-diyl dicarbonate; or dibutyl naphthalene-1,8-diyl dicarbonate.

12. The catalyst component of claim 1 which is optionally combined with a single component SCA, a mixed component SCA, or an activity limiting agent.

13. The catalyst component of claim 12 where the mixed component SCA contains an activity limiting agent or an organic ester as a component.

14. The catalyst component of claim 13 which is optionally combined with an organoaluminum compound.

15. A method of polymerizing an olefin comprising contacting the olefin with a catalyst component containing magnesium, titanium, and halogen, and further containing an internal electron donor having a structure:

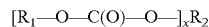

wherein $R_1$ is independently at each occurrence, an aliphatic or aromatic hydrocarbon, or substituted hydrocarbon group containing from 1 to 20 carbon atoms; x is 2-4; and $R_2$ is an aliphatic or aromatic hydrocarbon, or substituted hydrocarbon group containing from 1 to 20 carbon atoms, provided that there are from 3 to 4 atoms in the shortest chain connecting a first $R_1$—O—C(O)—O— group and a second $R_1$—O—C(O)—O— group.

16. A method of polymerizing an olefin comprising contacting the olefin with a catalyst component of claim 2.

17. A compound for use as an internal electron donor having a structure selected from the group consisting of:

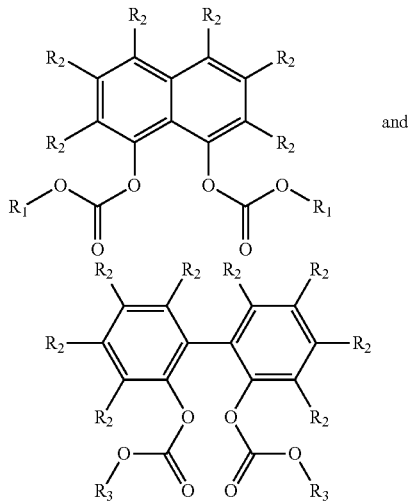

wherein $R_1$ is independently at each occurrence, an aliphatic or aromatic hydrocarbon, or substituted hydrocarbon group containing from 3 to 20 carbon atoms; $R_2$ is H or a $C_1$-$C_{20}$ hydrocarbon; and $R_3$ is a $C_1$-$C_{20}$ aliphatic hydrocarbon group.

18. The compounds of claim 17 wherein at least one $R_1$ group is an unbranched carbon chain.

* * * * *